US012674754B2

(12) United States Patent
Han et al.

(10) Patent No.: US 12,674,754 B2
(45) Date of Patent: Jul. 7, 2026

(54) METHOD FOR DETECTING TARGET BIOMOLECULE IN BIOLOGICAL SAMPLE, DISPOSABLE OPTICAL FIBER SENSOR THEREFOR, AND CARTRIDGE THEREOF

(71) Applicant: MBT Co., Ltd., Seoul (KR)

(72) Inventors: Byoung Don Han, Seoul (KR); Young Chul Choi, Daejeon (KR); Hee Baeg Choi, Seoul (KR); Hae Jin Lee, Seoul (KR); Kun Tahk Hwang, Seoul (KR)

(73) Assignee: MET Co., Ltd., Seoul (KR)

( * ) Notice: Subject to any disclaimer, the term of this patent is extended or adjusted under 35 U.S.C. 154(b) by 710 days.

(21) Appl. No.: 18/021,434

(22) PCT Filed: Aug. 25, 2021

(86) PCT No.: PCT/KR2021/011345

§ 371 (c)(1),
(2) Date: Feb. 15, 2023

(87) PCT Pub. No.: WO2022/045757

PCT Pub. Date: Mar. 3, 2022

(65) Prior Publication Data

US 2024/0035968 A1      Feb. 1, 2024

(30) Foreign Application Priority Data

Aug. 27, 2020    (KR) ........................ 10-2020-0108336
Aug. 27, 2020    (KR) ........................ 10-2020-0108337

(51) Int. Cl.
*G01N 21/552*    (2014.01)
*C12Q 1/6806*    (2018.01)
*C12Q 1/70*    (2006.01)
*G01N 1/10*    (2006.01)

(52) U.S. Cl.
CPC ......... *G01N 21/554* (2013.01); *C12Q 1/6806* (2013.01); *C12Q 1/70* (2013.01); *G01N 2001/1056* (2013.01)

(58) Field of Classification Search
CPC ......... G01N 21/554; G01N 2001/1056; G01N 2201/0221; G01N 33/48; C12Q 1/6806; C12Q 1/70; C12Q 1/6816; C12N 9/22; C12N 15/10
See application file for complete search history.

(56) References Cited

U.S. PATENT DOCUMENTS

2011/0150705 A1    6/2011    Doyle et al.
2017/0298426 A1    10/2017    Sardar et al.

FOREIGN PATENT DOCUMENTS

KR         10/1035230        5/2011
KR         10/1847745        4/2018
WO     WO-2019/104058 A1     5/2019

OTHER PUBLICATIONS

Kim et al., 2015 Transducers—2015, Anchorage, Alaska, pp. 265-268, Jun. 2015.*
Jeong et al., Biosensors and Bioelectronics, 39: 346-351 (Year: 2013).*
Petryayeva et al "Localized Surface Plasmon Resonance: Nanostructures, Bioassays and Biosensing—A Review" Analytica Chimica Acta vol. 706, pp. 8-24, 2011.
Tsou et al "A CRISPR Test for Detection of Circulating Nuclei Acids" Translational Oncology vol. 12, pp. 1566-1573, Dec. 2019.
Willets et al "Localized Surface Plasmon Resonance Spectroscopy and Sensing" Annual Review of Physical Chemistry vol. 58, pp. 267-297, 2007.

* cited by examiner

*Primary Examiner* — Cynthia B Wilder
(74) *Attorney, Agent, or Firm* — AJU IP Global PLLC

(57) ABSTRACT

Disclosed are: a method for detecting a target biomolecule in a biological sample, in which the method can be rapidly and inexpensively performed on site to diagnose diseases such as infectious diseases; an FO-LSPR optical fiber sensor which can be used therein; and a disposable sensor cartridge having the sensor mounted. The disposal sensor cartridge of the present invention can be used in the rapid detection of a target biomolecule, by mounting an optical fiber sensor and then connecting FO-LSPR equipment thereto. When an FO-LSPR molecular diagnostic system using the optical fiber sensor cartridge of the present invention is combined with a CRISPR-Cas system, target biomolecules can be detected accurately and conveniently without nucleic acid amplification.

5 Claims, 11 Drawing Sheets

Specification includes a Sequence Listing.

[Figure 1]
[Figure 2]
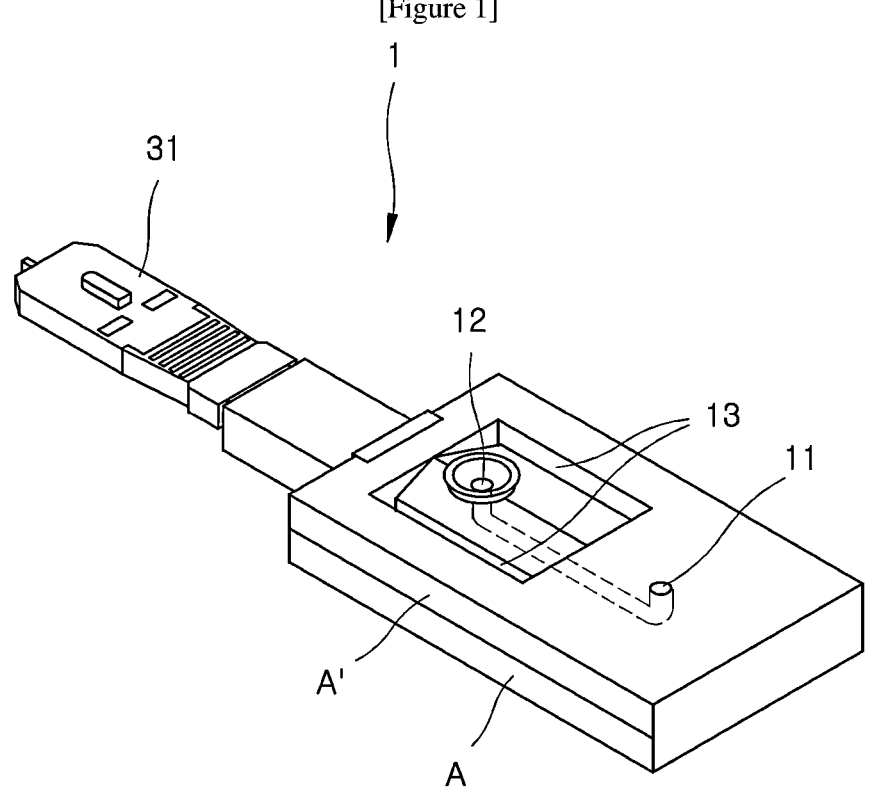

[Figure 3]
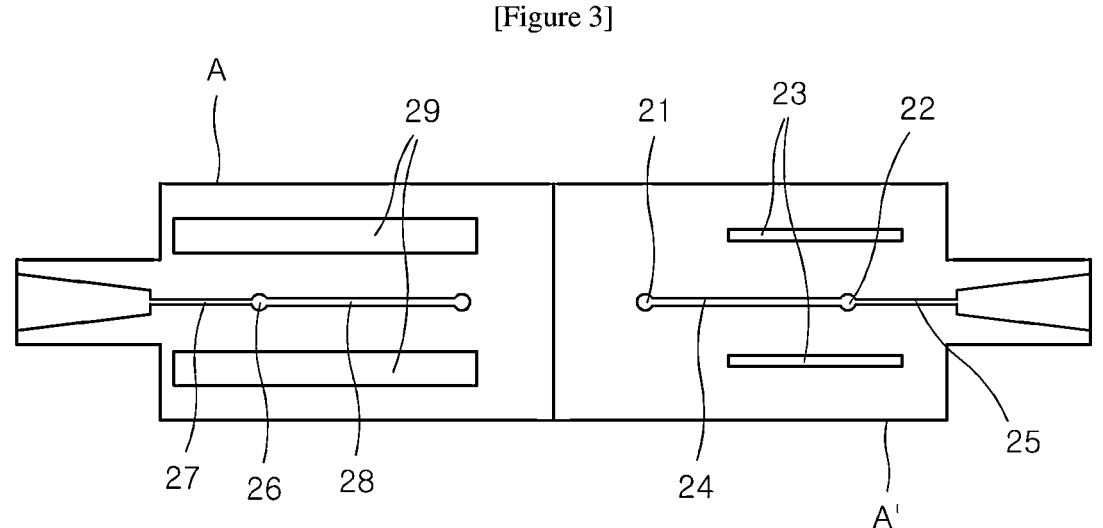

[Figure 4A]
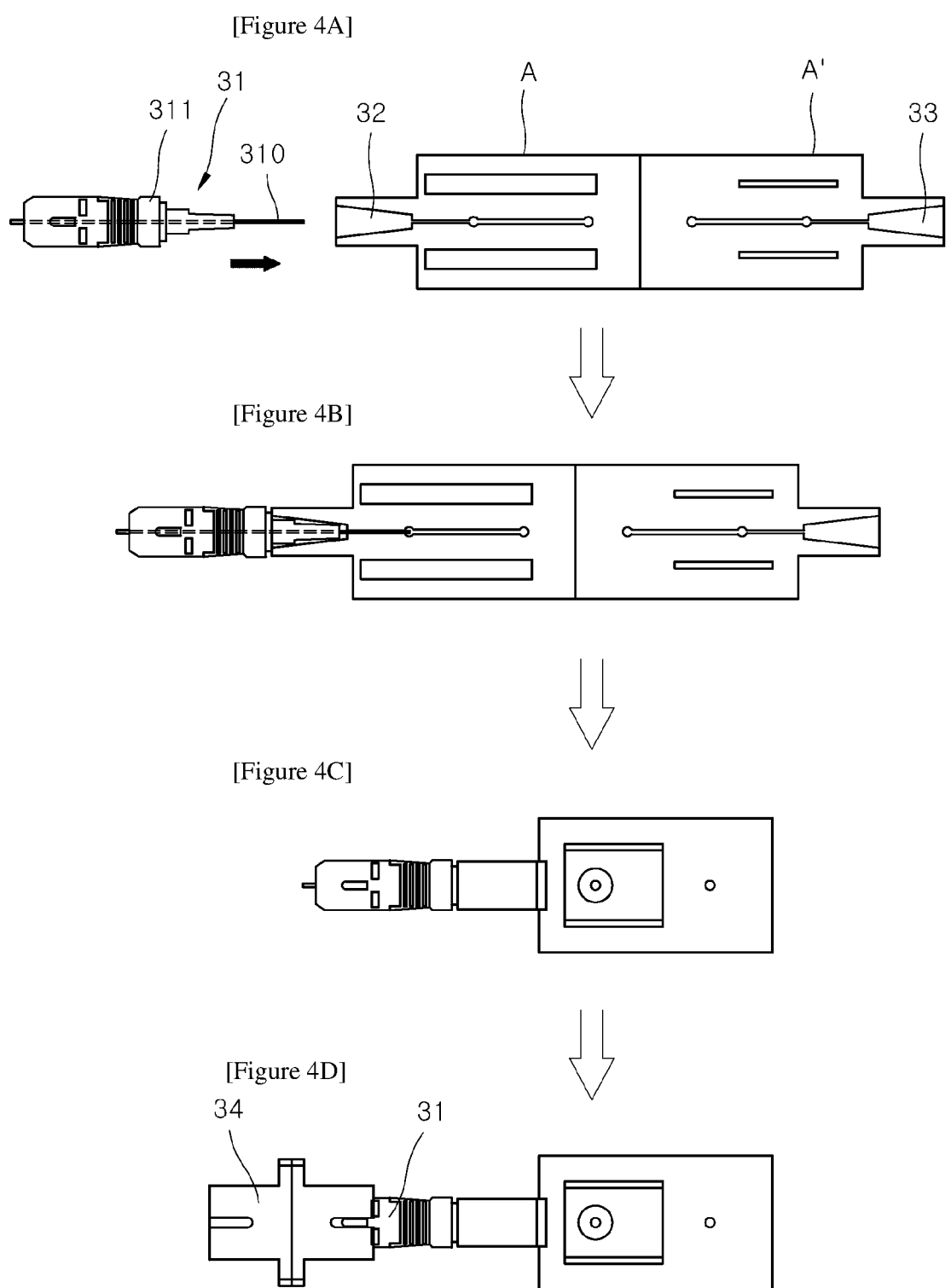
[Figure 4B]
[Figure 4C]
[Figure 4D]

[Figure 5]
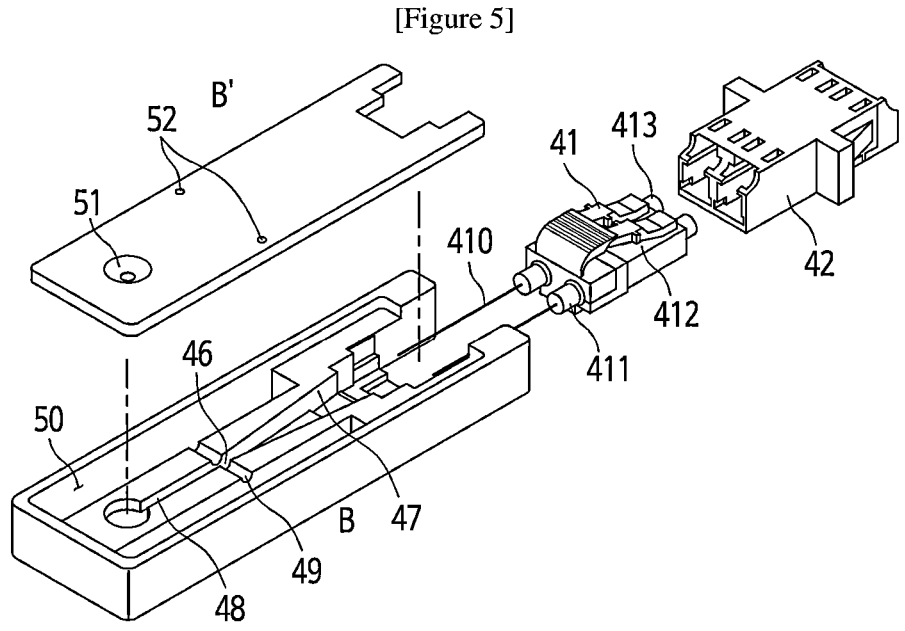
[Figure 6]
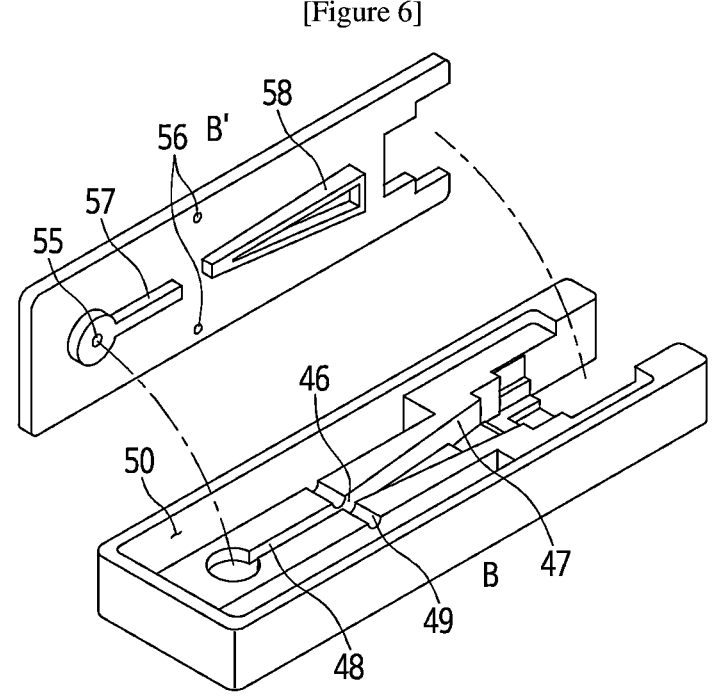

[Figure 7]
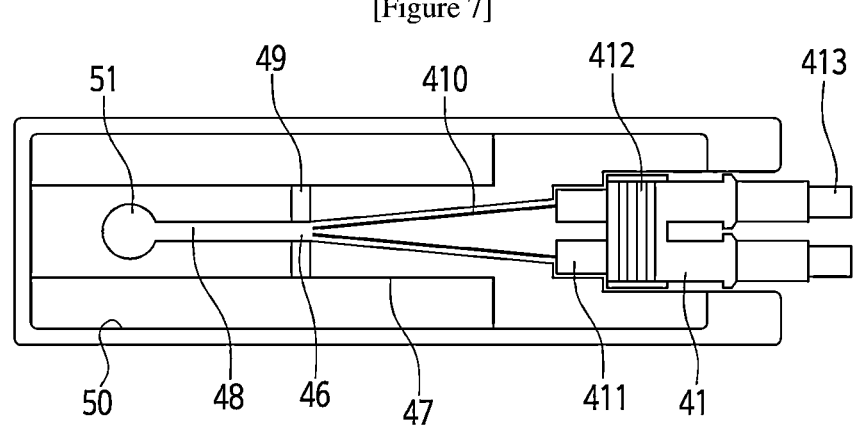
[Figure 8]
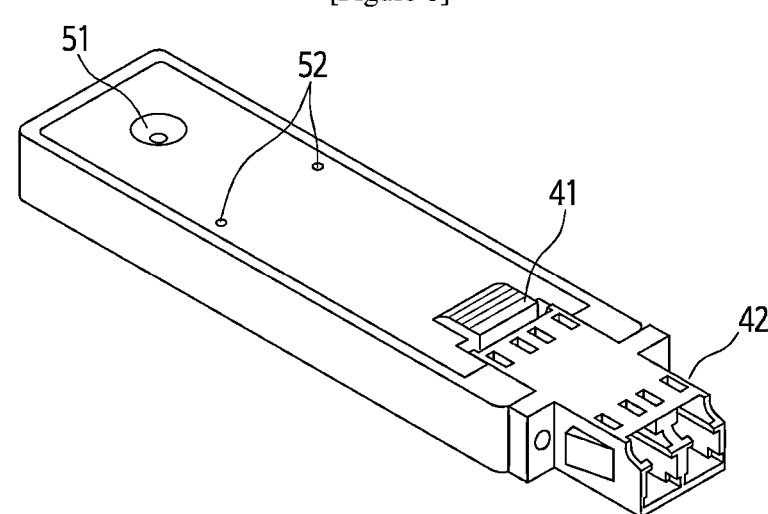

[Figure 9A]
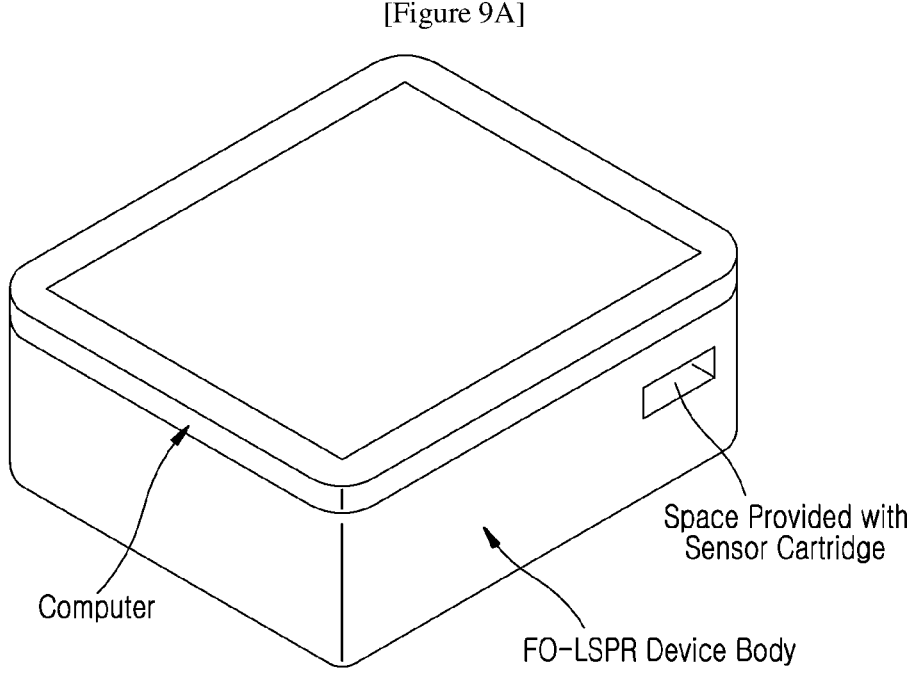
Computer
Space Provided with
Sensor Cartridge
FO-LSPR Device Body
[Figure 9B]
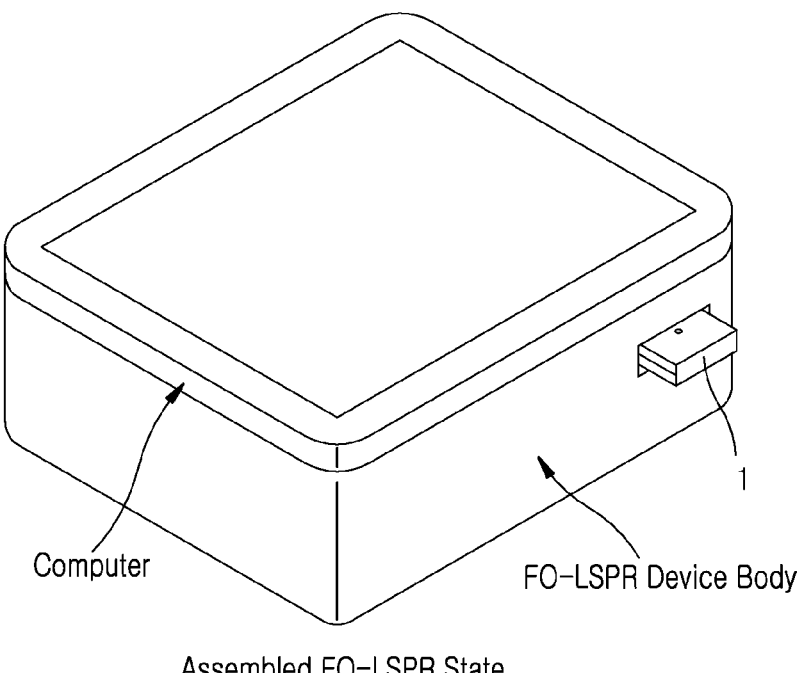
Computer
FO-LSPR Device Body
1
Assembled FO-LSPR State

[Figure 10]
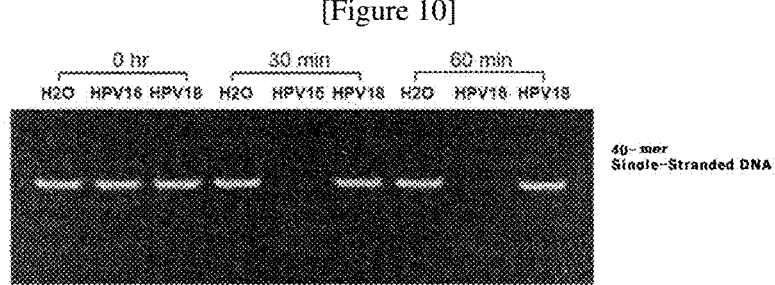
[Figure 11A]
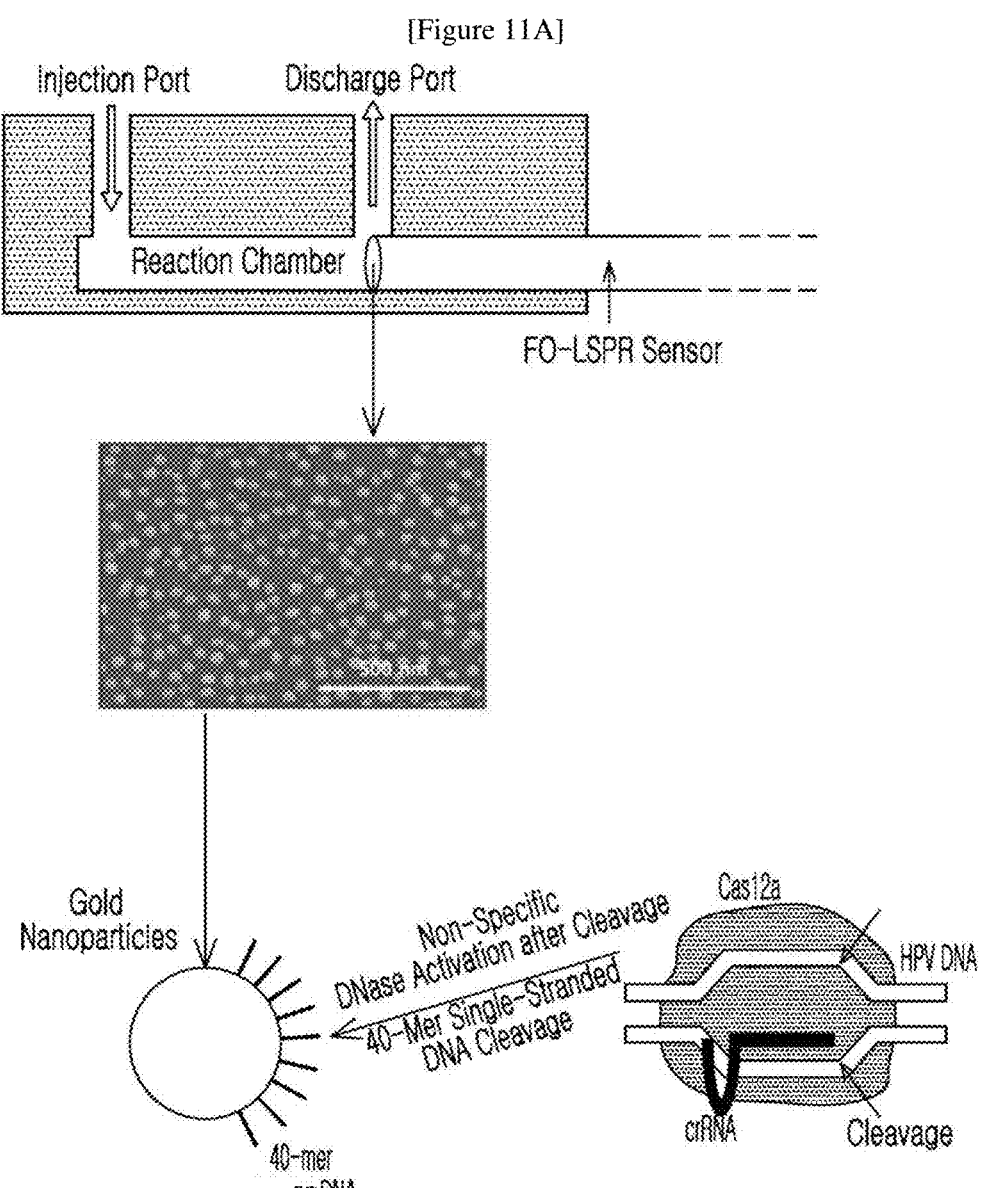

[Figure 11B]
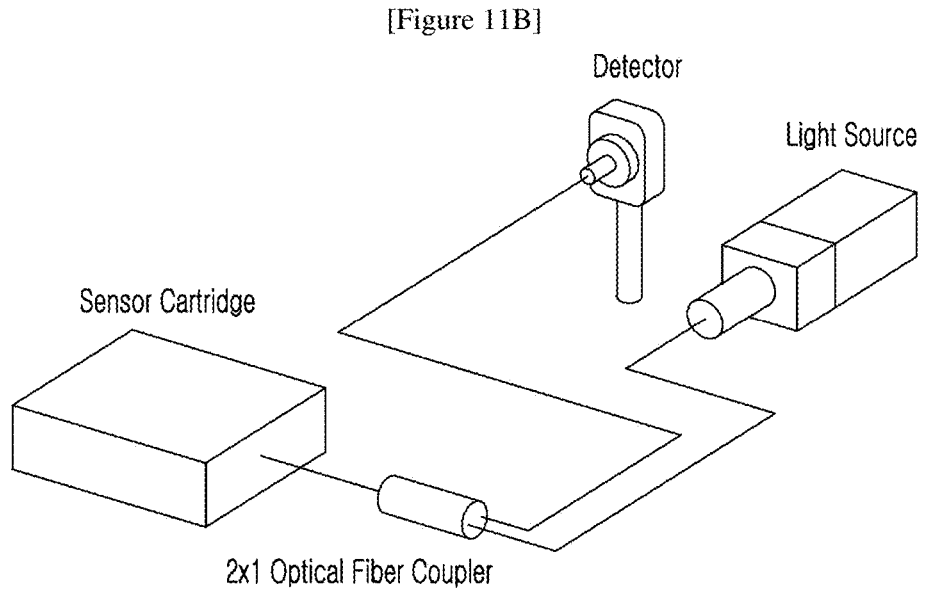
[Figure 12]
Trend Chart ΔI (mV) by Copy Number of HPV16
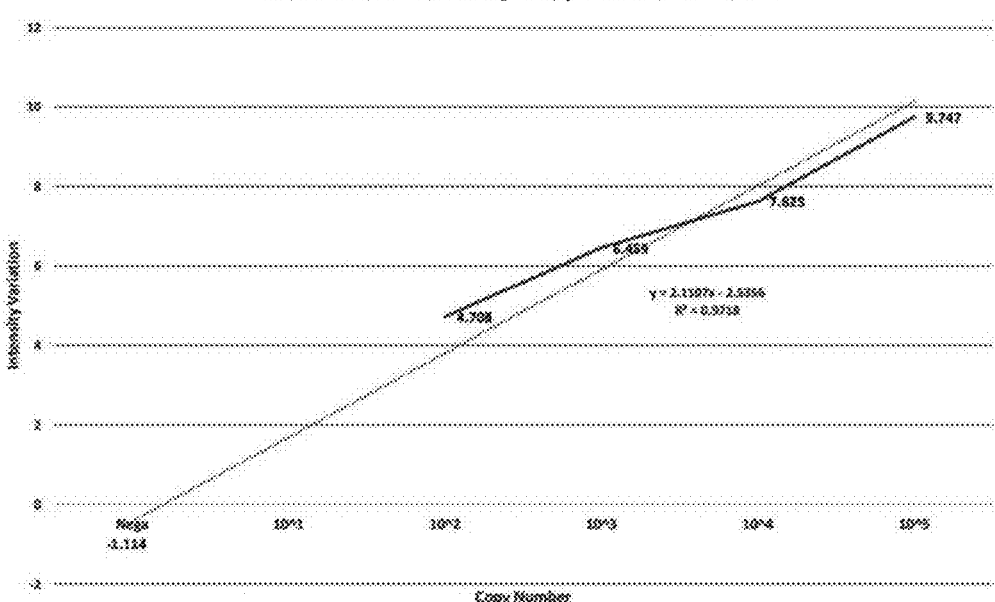

[Figure 13]
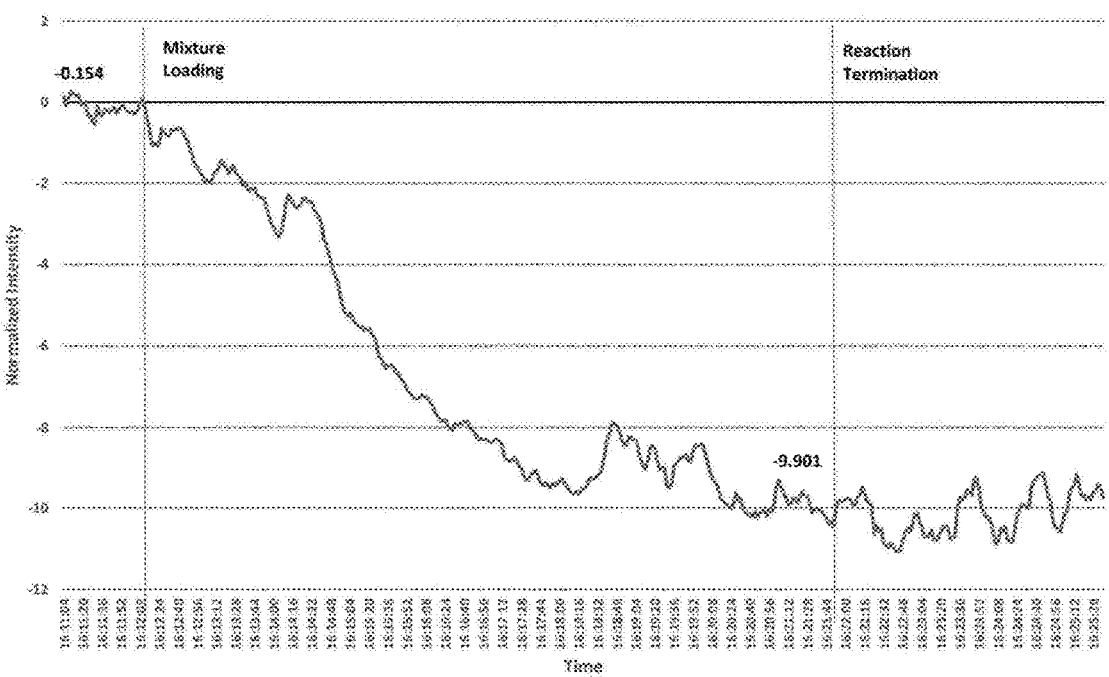
[Figure 14]
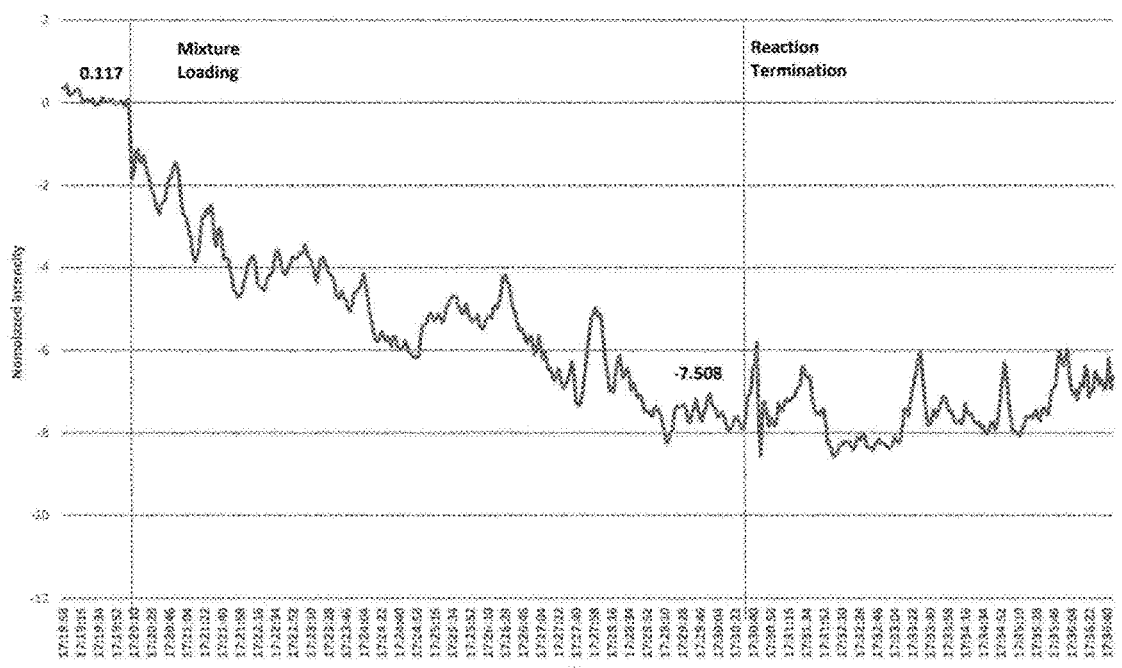

[Figure 15]
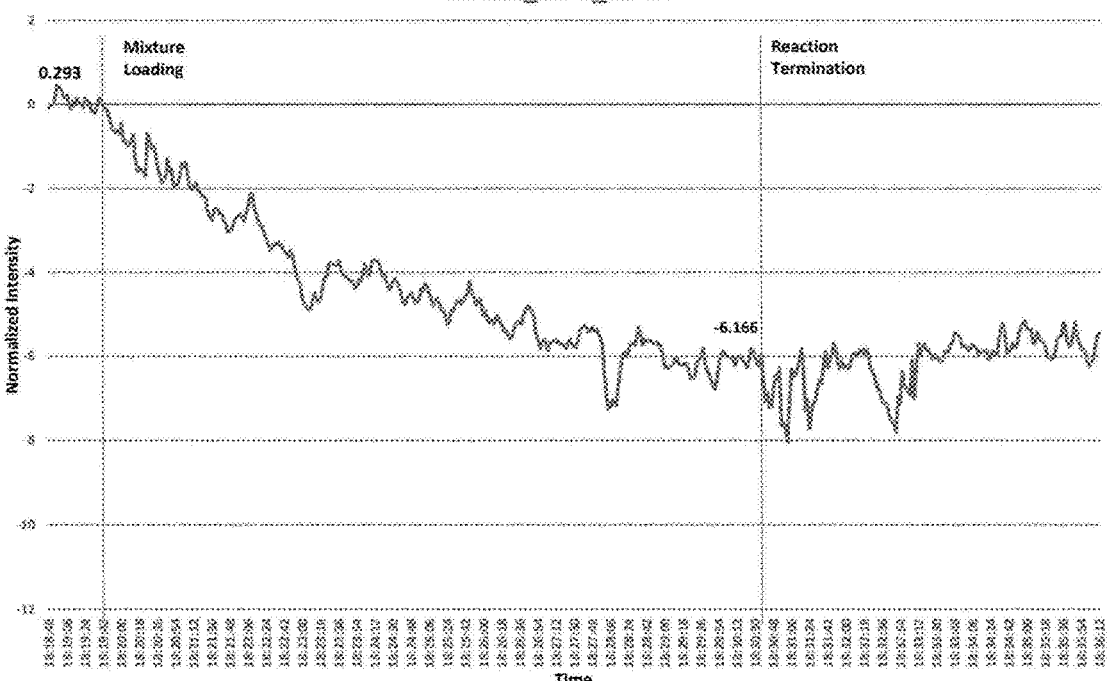
[Figure 16]
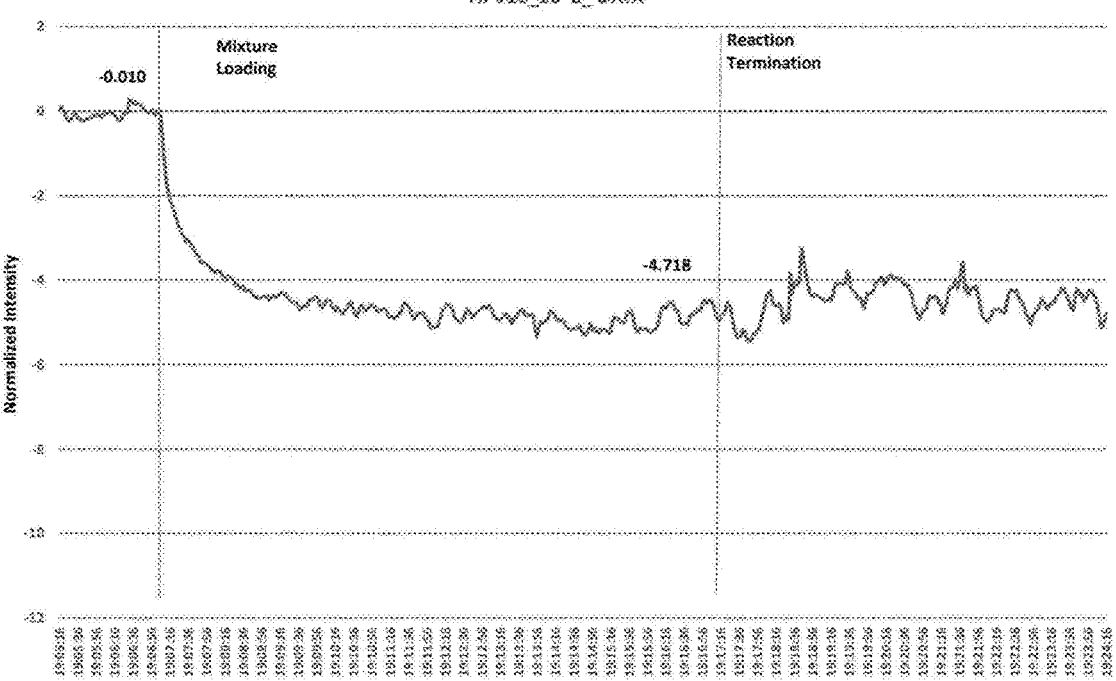

[Figure 17]
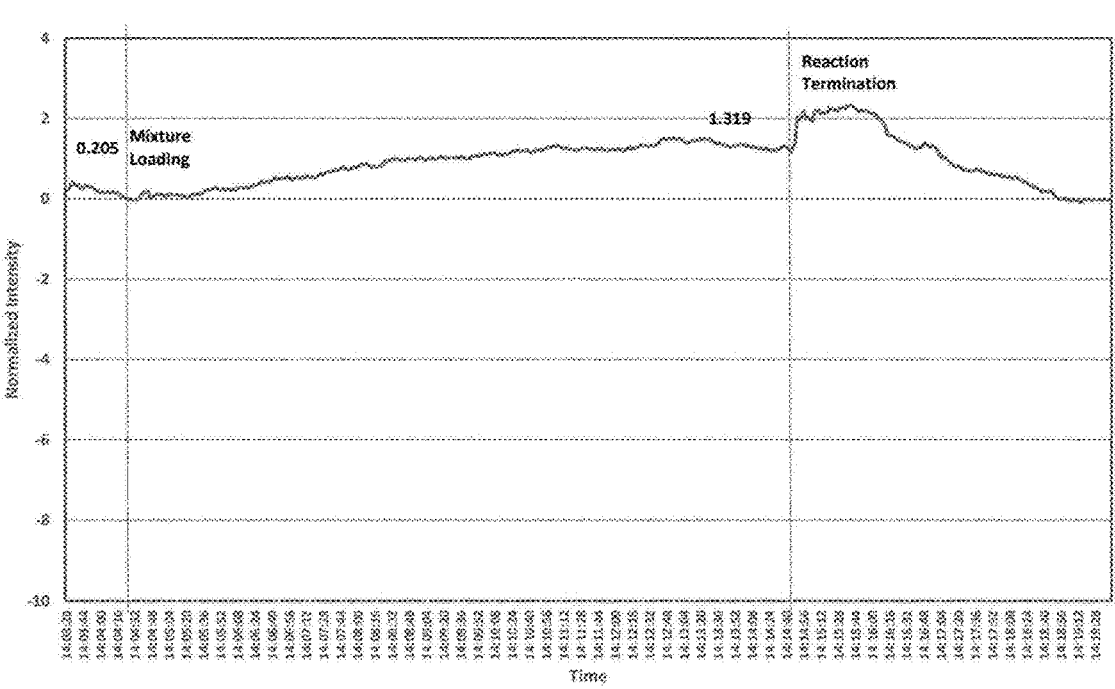

1

METHOD FOR DETECTING TARGET BIOMOLECULE IN BIOLOGICAL SAMPLE, DISPOSABLE OPTICAL FIBER SENSOR THEREFOR, AND CARTRIDGE THEREOF

CROSS-REFERENCE TO RELATED APPLICATIONS

This application is the national stage of International Patent Application No. PCT/KR2021/011345, filed on Aug. 25, 2021, which claims priority to Korean Patent Application No. 10-2020-0108336, filed on Aug. 27, 2020, and Korean Patent Application No. 10-2020-0108337, filed on Aug. 27, 2020, the entire contents of which are hereby incorporated by reference in their entirety.

TECHNICAL FIELD

The present invention relates to a method for detecting a target biomolecule in a biological sample, and more particularly, to a method for detecting a target biomolecule in a biological sample rapidly and conveniently using fiber optics-localized surface plasmon resonance (FO-LSPR) technology, a disposable sensor usable herein, and a cartridge thereof.

BACKGROUND

A biosensor is an analysis apparatus configured to detect a change in concentration or the presence of a biological material. In general, the biosensor is used for diagnosis by measuring a physicochemical change caused by attaching a ligand, to which biomolecules such as protein antigens, nucleic acids, or the like can bind, to a sensor and allowing a biological material to bind to the ligand. Such a physicochemical change includes an electrochemical, surface plasmon resonance (SPR), localized surface plasmon resonance (LSPR), field effect transistor (FET), fluorescence, quartz crystal microbalance (QCM) changes, and the like.

Localized surface plasmon resonance (LSPR) is a phenomenon in which electrons vibrate collectively due to the interaction between light and electrons at the interface between a metal surface and a dielectric when fine metal nanoparticles are irradiated with light (Willets and Van Duyne, Annu rev Phys Chem 58:267-297, 2007; Petryayeva and Krull, Anal Chim Acta., 706: 8-24, 2011). When biomolecules are fixed on surfaces of the metal nanoparticles and other molecules capable of binding to the biomolecules are bound to the biomolecules, a reflective index of a surrounding medium is changed, and a wavelength at which resonance occurs is changed accordingly. In this case, a sensor may detect such a change to analyze a sample.

A diagnostic method of detecting certain pathogens or viruses in infectious diseases, may include an immunodiagnostic method and a molecular diagnosis method. Representative technology for the molecular diagnosis method is polymerase chain reaction (PCR) that has been widely used for the detection of nucleic acids. However, this method has drawbacks in that it is necessary to manipulate a sample, is expensive and time-consuming, and requires large equipment and high risk of contamination during sample manipulation. Those factors make it difficult as a point-of-care testing (POCT).

Therefore, there is a need for development of a method capable of simple sample manipulation for point-of-care testing (POCT) and rapid detection of a target material without any need for large equipment, or a device capable of implementing such a method.

The present inventors have attempted to meet the requirements in the related art by developing a disposable optical fiber sensor cartridge capable of being used in conjunction with small-scale diagnostic equipment used in the field.

RELATED ART DOCUMENT

KR Patent No. 10-1847745

DISCLOSURE

Technical Problem

Therefore, it is an object of the present invention to provide a method for analyzing a sample, which may be rapidly performed in the field at a low cost in order to diagnose infectious diseases.

It is another object of the present invention to provide a method for specifically detecting a target nucleic acid in a biological test sample when CRISPR-Cas technology is combined with biosensor technology.

It is still another object of the present invention to provide a disposable optical fiber sensor that may be used in combination with a small-scale optical detection device in order to diagnose infectious diseases, and a cartridge thereof.

It is yet another object of the present invention to provide a molecular diagnosis system for specifically detecting a target material in a biological test sample.

Technical Solution

According to an aspect of the present invention, there is provided a method for detecting a target nucleic acid in a test sample, which includes:

a) contacting a CRISPR RNA, which binds to a target nucleic acid, and a Cas protein with a test sample isolated from the living body so that the CRISPR RNA and the Cas protein are allowed to react with the test sample;

b) contacting the reaction product with a fiber optics-localized surface plasmon resonance (FO-LSPR) sensor containing metal nanoparticles having a nucleic acid oligomer attached thereto; and c) irradiating the sensor with light to measure an intensity change value of an FO-LSPR output signal.

According to one embodiment of the present invention, the target nucleic acid may be dsDNA, ssDNA, or ssRNA.

According to one embodiment of the present invention, the Cas protein may be selected from the group consisting of Cas12a, Cas13a, and Cas14.

According to one embodiment of the present invention, the Cas protein may be Cas12a, the CRISPR RNA may have a base sequence set forth in SEQ ID NO: 1, and the target nucleic acid may be HPV16 dsDNA. The CRISPR RNA may be 41-mer single-stranded RNA, and a 21-mer sequence of the 5' end of the RNA molecule may be a region that binds to Cas12a, and a 20-mer sequence of the 3' end may bind to a target nucleic acid, that is, a L1 region of HPV16 genomic dsDNA.

According to one embodiment of the present invention, the nucleic acid oligomer may be a universal oligomer that may be used regardless of the sequence of the target nucleic acid.

For example, the universal oligomer may be a 40-mer single-stranded DNA that has a sequence containing eight TTTTA repeats. In this case, streptavidin, biotin, or the like may be attached to the 40-mer single-stranded DNA to increase the molecular weight of the 40-mer single-stranded DNA, thereby inducing a change in an output signal intensity value to enhance sensitivity.

According to one embodiment of the present invention, the method may further include comparing the output signal intensity value with an FO-LSPR output signal value from a control sample.

According to one embodiment of the present invention, the CRISPR RNA may be a mixture of RNAs that are able to bind to several sites of the target nucleic acid, respectively.

According to another aspect of the present invention, there is provided a disposable sensor cartridge for mounting an optical fiber sensor member, which includes:

a cartridge body having a reaction chamber, a sensor insertion groove, a fluid passage, and a waste reservoir formed therein; and a cartridge cover having a sample injection port and a fluid discharge port formed therein.

According to one embodiment of the present invention, the cartridge may include a cartridge body including a reaction chamber, a first sensor insertion groove, a first fluid passage, and a waste reservoir; and a cartridge cover having a sample injection port, a sample discharge port, and a waste inlet configured to introduce a fluid flowing through the sample discharge port into the waste reservoir formed in a top surface thereof, and having a second fluid passage corresponding to the first fluid passage, a waste inlet, and a second sensor insertion groove corresponding to the first sensor insertion groove formed in an opposite surface thereof.

The inflow of the fluid into the waste reservoir may be caused when a portion of a top surface of the cover including a portion of the sample discharge port is formed as an inclined surface.

According to one embodiment, the cartridge may include a cartridge body having a reaction chamber, a sensor insertion groove, a fluid passage, a connection passage, and a waste reservoir formed therein; and a cartridge cover having a sample injection port and an air discharge port formed on a top surface thereof, and having a first protrusion corresponding to the fluid passage and a second protrusion corresponding to the sensor insertion groove formed on an opposite surface thereof.

According to one embodiment, the cover and the body of the sensor cartridge may be folded or separated from each other.

According to one embodiment, a groove in which the optical fiber sensor member is disposed may be further formed in the body and/or cover of the cartridge.

According to still another aspect of the present invention, there is provided an optical fiber sensor member mounted in the sensor cartridge as described above.

According to one embodiment, one or more optical fibers may be included in the optical fiber sensor member. Metal nanoparticles to which a DNA oligomer, an RNA oligomer, an antigen, or an antibody is attached may be bound to an end of the optical fibers, depending on the type of target biomolecule to be detected.

According to one embodiment, when two optical fibers are included in the optical fiber sensor member, the optical fiber sensor member may be an optical fiber sensor member in which metal nanoparticles to which an ssDNA oligomer is attached are bound to an end of one optical fiber, and metal nanoparticles to which an ssRNA oligomer is attached are bound to an end of the other optical fiber.

According to one embodiment, the metal nanoparticles attached to the optical fiber are not particularly limited as long as surface plasmon resonance or surface-enhanced Raman scattering takes place. For example, the metal nanoparticles may be made of gold or silver, and may have a spherical, rod-type or star-like irregular shape. For example, the metal nanoparticles may be spherical gold nanoparticles having a size of approximately 50 nm.

According to yet another aspect of the present invention, there is provided a molecular diagnosis system, which includes an FO-LSPR optical fiber sensor to which a nucleic acid oligomer cleavable by the action of a CRISPR-Cas system is attached.

According to one embodiment, the nucleic acid oligomer cleavable by the action of the CRISPR-Cas system may be attached to the optical fiber sensor member of the present invention.

According to yet another aspect of the present invention, there is provided a biomolecular diagnosis system using the FO-LSPR, which includes the disposable sensor cartridge of the present invention, and an optical fiber sensor member mounted in the disposable sensor cartridge.

Advantageous Effects

When a CRISPR-Cas system is combined with an FO-LSPR molecular diagnosis system using an optical fiber sensor and the cartridge of the present invention, a target biomolecule can be detected accurately and conveniently without a nucleic acid amplification process. A disposable sensor cartridge provided in the present invention can be used to diagnose infectious diseases by mounting an optical fiber sensor and then connecting FO-LSPR equipment to the optical fiber sensor to detect a target biomolecule. The sensor cartridge of the present invention can be easily used because the sensor cartridge is easily attached and detached to/from the FO-LSPR equipment, and is easily mass-produced at low production costs because the sensor cartridge is made of plastic materials.

DESCRIPTION OF DRAWINGS

FIGS. 1 and 2 are schematic diagrams showing an assembled state of a sensor cartridge 1 and an optical fiber sensor member 31 in a state in which a cover A' and a body A according to one embodiment of the present invention are folded.

FIG. 3 is a schematic diagram showing the names of respective parts of the body A and the back side of the cover observed when the cover A' of the sensor cartridge according to one embodiment of the present invention is unfolded.

FIGS. 4A-4D are a schematic diagram showing processes of mounting an optical fiber sensor member 31 in a sensor cartridge according to one embodiment of the present invention, closing a cover, and connecting an adaptor 34 to the other end of the sensor member 31 in a sequential manner.

FIG. 5 is a schematic diagram showing the relationship in which an optical fiber sensor member 41 and an adaptor 42 are connected to sensor cartridges B and B' according to one embodiment of the present invention.

FIG. 6 is a perspective view showing the sensor cartridge body B and the back side of the cover B' according to one embodiment of the present invention.

FIG. 7 is a schematic diagram showing an aspect in which the optical fiber sensor member 41 is mounted in the sensor cartridge body B according to one embodiment of the present invention, as viewed from above.

FIG. 8 is a schematic diagram showing an aspect in which the sensor cartridges B and B', the optical fiber sensor member 41, and the adaptor 42 are assembled according to one embodiment of the present invention.

FIGS. 9A and 9B are a schematic diagram showing an aspect in which the sensor cartridge according to one embodiment of the present invention is inserted into a body case of FO-LSPR equipment, which includes a computer equipped with a laser light source, a detector, and a signal analysis program, and then applied.

FIG. 10 is an electrophoresis gel image showing that a substrate, 40-mer ssDNA, is cleaved by the non-specific DNase activity induced after Cas12a and crRNA recognizes and cleaves a target HPV16 DNA sequence according to one embodiment of the present invention. It is deduced that the non-specific DNase activity is induced due to the presence of the target HPV16 DNA corresponding to crRNA because the 40-mer ssDNA is not cleaved when HPV18 DNA is added as the target nucleic acid, and is cleaved only when HPV16 DNA is added.

FIG. 11A is a diagram simplifying a lower inner part of a portable cartridge in which an optical fiber sensor according to one embodiment of the present invention is positioned. In the portable cartridge, an end of an optical fiber is positioned in a reaction chamber and the other end of the optical fiber is connected to an adaptor, and thus may be connected to FO-LSPR equipment present at a rear end of the portable cartridge. Metal nanoparticles may be attached to an end surface of an optical fiber positioned in the reaction chamber by electrostatic interaction, and for example, 40-mer ssDNA, which is a substrate of Cas12a, may be attached to the metal nanoparticles. When a sample and a Cas protein are injected through an injection port, a structural change of the 40-mer ssDNA may be caused based on the presence or absence of a target nucleic acid in the sample. As a result, the presence of the target nucleic acid may be detected through a change in output intensity at the FO-LSPR equipment present at the rear end of the portable cartridge.

FIG. 11B is a schematic diagram showing that a sensor cartridge in which the optical fiber sensor is mounted is connected to the FO-LSPR equipment including a detector and light source positioned at the rear end thereof, according to one embodiment of the present invention.

FIG. 12 shows a net change in output intensity value of an optical fiber depending on the copy number of HPV16 DNA, as measured by the FO-LSPR equipment according to one embodiment of the present invention.

FIGS. 13 to 17 sequentially show sensograms of CRISPR-Cas12a trans-cleavage activities varying according to an amount of HPV16 DNA having a copy number of $10^5$, $10^4$, $10^3$, $10^2$ and 0 in a reaction solution, as measured by the FO-LSPR equipment according to one embodiment of the present invention.

DETAILED DESCRIPTION

Hereinafter, preferred embodiments of the present invention will be described in detail to illustrate the configuration and action of the present invention. However, it should be understood that the preferred embodiments of the present invention are provided for illustrative purposes only and are not intended to limit the present invention in any way.

Contents not described herein can be technically inferred by those skilled in the art to which the present invention belongs, and thus a description thereof will be omitted.

In the present invention, the term "diagnosis" refers to a process of determining the presence or absence of a disease, or bacteria or viruses associated with the disease.

In the present invention, the term "detection" includes quantitative and/or qualitative analysis, that is, detection of the presence or absence of a material, and detection of an amount (level) of the material when present.

In the present invention, the term "test sample" refers to a biological sample isolated from a subject, or a liquid-phase fluid including the sample. For example, the test sample includes blood, saliva, urine, and a post-nasal mucous secretion isolated from a subject.

In the present invention, the term "fluid" includes a test sample, a buffer, a washing solution, or air.

One aspect of the present invention relates to a molecular diagnosis method that detects the presence of bacteria or viruses with high sensitivity by specifically recognizing a nucleic acid of a target pathogen or a virus using a CRISPR-Cas system, inducing a structural change (such as cleavage, and the like) by allowing induced Cas nuclease activity to act on an oligomer provided in a fiber optics-localized surface plasmon resonance (FO-LSPR) sensor, and detecting the induced change using the FO-LSPR sensor to send signals to LSPR equipment.

In FO-LSPR, the wavelength or intensity of light that is absorbed and scattered is changed depending on a change in medium surrounding a metal. Using this, the occurrence or extent of an expected reaction may be detected by measuring a fine change in reflective index of incident light in an optical fiber, a change in LSPR wavelength, or a change in output intensity of the sensor depending on the changes in the surrounding environment of a metal (for example, an antigen binding to an antibody, DNA hybridization, cleavage of substrate DNA attached to the sensor by DNase, or the like).

Therefore, according to one embodiment of the present invention, the presence or absence of the target nucleic acid may be determined by checking a change in output signal intensity value of the sensor induced when the nucleic acid oligomer attached to the optical fiber sensor is cleaved by the activated Cas protein.

For example, when the Cas protein is Cas12a, it binds to CRISPR RNA. Then, when this complex binds to the target DNA of a pathogen which is complementary to a sequence of the CRISPR RNA, Cas12a is activated to cleave the target DNA. When the target DNA is cleaved, the DNase activity of the Cas12a protein may be induced to cleave a nucleic acid oligomer, which is a substrate attached to the sensor, regardless of the sequence of ssDNA (FIG. 10).

When various types of CRISPR RNAs recognizing different regions of the target nucleic acid are prepared and reacted together with Cas12a, the non-specific DNase activity of Cas12a may be further increased if there is a target nucleic acid.

Meanwhile, when Cas12a protein cleaves dsDNA as the target nucleic acid, its sequence non-specific DNase activity is activated after the cleavage. When the Cas13a protein cleaves ssRNA as the target nucleic acid, its RNase activity is activated after the cleavage. When the Cas14 cleaves ssDNA as the target nucleic acid, its DNase activity is activated after the cleavage. Therefore, Cas proteins may be selected and used for the reaction, depending on the type of target nucleic acid to be detected.

In the method of the present invention, a base sequence of the CRISPR RNA is designed differently depending on the type of target pathogen or virus, and a nucleic acid oligomer attached to the optical fiber sensor can be universally used.

The optical fiber sensor of the present invention may be used to extend the range of application for the diagnosis of infectious diseases caused by microbes because the optical fiber sensor can be combined with the Cas protein to detect all types of dsDNA, ssRNA, and ssDNA as the target nucleic acid of a pathogen or virus.

The method of the present invention may further include comparing the output signal intensity value with an FO-LSPR output signal value measured from a control sample. The control sample is a sample without a target nucleic acid, for example, a sample of a patient whose disease has been completely cured, a simple buffer, or the like.

Another aspect of the present invention relates to an FO-LSPR optical fiber sensor member capable of being used in the above-described method for detecting a target biomolecule, and a sensor cartridge capable of mounting the same.

One embodiment of the present invention is a disposable sensor cartridge for mounting the optical fiber sensor member. Here, the sensor cartridge includes a cartridge body having a reaction chamber, a sensor insertion groove, a fluid passage, and a waste reservoir formed therein, and a cartridge cover having a sample injection port and a fluid discharge port formed therein. The sensor cartridge is used for the rapid detection of a target biomolecule for diagnosing infectious diseases in conjunction with the optical fiber sensor and the FO-LSPR equipment.

According to one embodiment, the sensor cartridge may include a cartridge body A having a reaction chamber 26, a first sensor insertion groove 27, a first fluid passage 28, and a waste reservoir 29 formed therein; and a cartridge cover A' having a sample injection port 11, a sample discharge port 12, and a waste inlet 13 configured to introduce a fluid flowing from the sample discharge port into the waste reservoir formed in a top surface thereof, and having a second fluid passage 24 corresponding to the first fluid passage, a waste inlet 23, and a second sensor insertion groove 25 corresponding to the first sensor insertion groove formed in an opposite surface thereof. The inflow of the waste fluid into the reservoir may be caused when a portion of a top surface of the cover including a portion of the sample discharge port is formed as an inclined surface.

According to one embodiment, the sensor cartridge may include a cartridge body B having a reaction chamber 46, a sensor insertion groove 47, a fluid passage 48, a connection passage 49, and a waste reservoir 50 formed therein; and a cartridge cover B' having a sample injection port 51 and an air discharge port 52 formed in a top surface thereof, and having a first protrusion 57 corresponding to the fluid passage 48 and a second protrusion 58 corresponding to the sensor insertion groove 47 formed in an opposite surface thereof. Here, a protruding height of the first protrusion 57 may be formed to a level of approximately 70% to 90% of a depth of the fluid passage. When a reaction washing solution is introduced into the lower part of the reaction chamber 46 through the fluid passage 48 due to the structure having the protrusions, fluid exchange may occur more easily by pushing up a fluid present at the center of the reaction chamber. The second protrusion 58 may serve to hold two strands of optical fibers positioned in the sensor insertion groove 47, prevent erroneous fluid overflow in the reaction chamber 46, and fix the cartridge body and cover.

According to one embodiment, the cover and body of the sensor cartridge may be in a folded state. In this case, when the cover is folded over the body, the back side of the cover and the body are in contact with each other at facing positions to form a complete space or passage (FIGS.

4A-4D). For example, the first fluid passage 28 of the cartridge body and the second fluid passage 24 in the back side of the cover are in contact with each other to form a complete fluid passage, and the first sensor insertion groove 27 of the body and the second sensor insertion groove 25 in the back side of the cover are in contact with each other to form a complete sensor insertion groove.

Respective parts of the body and/or the back side of the cover of the sensor cartridge according to the present invention may be formed in an engraved manner, except the openings or protrusions.

According to one embodiment, the cover and the body may be separated from each other (FIG. 5). In this case, the cover and the body may be coupled by means of a connection part, or may be coupled with the corresponding concave-convex regions.

According to one embodiment, a groove in which the optical fiber sensor member is disposed may be further formed in the body and/or cover of the sensor cartridge.

The flow of a fluid in the sensor cartridge of the present invention is as follows.

When a fluid is injected through the sample injection port 11 or 51 in a state in which the cover of the sensor cartridge is closed, the fluid is collected in a region of the body corresponding to the sample injection port of the cover, and then moves to the reaction chamber 26 or 46 through the fluid passage. According to one embodiment, the fluid comes into contact with an end of an optical fiber positioned in the reaction chamber 26 or 46, and then moves to the waste reservoir 29 through the sample discharge port 12. According to another embodiment, the fluid comes into contact with an end of an optical fiber, and then moves to the waste reservoir 50 via the connection passage 49. In this case, the air that may be injected into the cartridge together with the sample flows out through the air discharge port 52. The waste reservoir 29 or 50 is a region configured to store excess fluid passing through the reaction chamber. In this case, nucleic acids or antigens, which do not participate in the reaction of the optical fiber sensor with a reporter molecule, may be removed through the waste reservoir 29 or 50 by injecting a washing solution thereinto.

One embodiment of still another aspect of the present invention is an optical fiber sensor member 31 or 41 mounted in the above-described sensor cartridge.

According to one embodiment, one optical fiber may be included in the optical fiber sensor member 31.

According to one embodiment, two optical fibers may be included in the optical fiber sensor member 41.

As shown in FIGS. 4A-4D and 7, the optical fiber sensor member is mounted in the sensor cartridge so that an exposed end of an optical fiber is positioned inside the reaction chamber of the sensor cartridge. Metal nanoparticles to which the reporter molecule is attached may be electrostatically coupled to an end of the optical fiber. For example, the metal nanoparticles may be spherical gold or silver nanoparticles having a size of approximately 50 nm.

The reporter molecule serves as an indicator for the reaction in the reaction chamber, and includes DNA, RNA, an antigen, an antibody, and the like, which may be structurally changed by cleavage, binding, and the like depending on the presence of the target material in the sample. For example, the target material may be DNA, RNA, an antigen, or an antibody, which is derived from a certain pathogen or virus.

For example, when diagnosing a malaria infection, an $HRP_2$ or LDH antigen may be used as the target material. When diagnosing tuberculosis, a CFP-10 antigen may be used as the target material. In this case, an antibody against the antigen may be used as the reporter molecule.

For example, when a target material to be detected is dsDNA and is detected using a CRISPR-Cas12a system, a reporter molecule attached to the metal nanoparticles binding to an end of an optical fiber of the optical fiber sensor member may be ssDNA. In this case, when the complex of Cas protein and CRISPR RNA specifically binds to target DNA having a base sequence complementary to the CRISPR RNA in a test sample to cleave the target DNA, the non-specific DNase activity of Cas12a may be induced to cleave ssDNA attached to the metal nanoparticles of the optical fiber sensor. In this case, FO-LSPR equipment may sense this change to confirm the presence of the target material.

When two optical fibers are included in the optical fiber sensor member, one strand of the optical fibers may be used as the control to easily determine whether the system is normally operating.

For example, when detecting a dsDNA virus using CRISPR-Cas12a, an ssDNA oligomer on which activated Cas12a acts may be attached to surfaces of the metal nanoparticles at the end of one optical fiber, and an ssRNA oligomer on which activated Cas13a acts may be attached to surfaces of the metal nanoparticles at the end of the other optical fiber. It can be checked, along with whether or not a target material is detected, whether the system is normally operated by designing crRNA, which corresponds to molecules (housekeeping genes such as GAPDH, beta-actin, and the like) always present in a biological sample, to activate Cas13a (in an actual experiment, a sample, and Cas12a and Cas13a can be added together and reacted in one tube), and allowing the activated Cas13a to cleave an ssRNA oligomer attached to an optical fiber in order to send LSPR signals when the activated Cas13a is brought into contact with an optical fiber sensor.

When detecting an RNA virus as a target material using CRISPR-Cas13a, a reporter molecule attached to the metal nanoparticles present at the ends of two optical fibers may be configured opposite to that described above.

According to one embodiment, the optical fiber sensor member 31 has a support 311 through which an optical fiber 310 passes. In this case, the support serves to support the optical fiber, and connect the optical fiber to an adaptor 34 present at a rear end of the optical fiber sensor member 31 as well. When this member is mounted in a groove 32 corresponding to the sensor cartridge so that the end of the optical fiber is positioned inside the reaction chamber, the exposed optical fiber is positioned in the sensor insertion groove 27 (FIGS. 4A-4D).

According to one embodiment, the optical fiber sensor member 41 has support 412 through which an optical fiber 410 passes. In this case, the support serves to support the optical fiber, and connect the optical fiber to an adaptor 42 present at a rear end of the optical fiber sensor member 41 as well. When an optical fiber sensor member is mounted in the cartridge so that the end of the optical fiber is positioned inside the reaction chamber 46, the exposed optical fiber is positioned in the sensor insertion groove 47 (FIG. 7). The optical fiber sensor member may further include a guide 411 configured to maintain a gap between two optical fibers in the cartridge body. When the optical fiber sensor member 41 having two optical fibers is mounted in the cartridge body, the two optical fibers coming out of the guide are disposed to converge towards the reaction chamber 46.

The connection of the adaptor 42 to the optical fiber sensor member 41 may be made after a protective cap 413 configured to protect the other end of the optical fiber passing through the support 412 is removed. The support 412 may be easily connected to the adaptor because the support 412 has a shape or structure that engages with the adaptor 42 present at a rear end of the optical fiber sensor member 41.

The support, the guide, and the protective cap may be made of generic plastic materials. For example, the member may be shaped using polystyrene, polytetrafluoroethylene, PVC, polypropylene, polyethylene, polycarbonate, polyethylene terephthalate, and the like, and the plastic material is not limited thereto.

Commercially available multi-mode optical fibers may be used as the optical fibers 310 or 410 of the optical fiber sensor member 31 or 41.

The adaptor is connected to an optical fiber connection member (for example, an SC/PC connector) so that the light source and the detector present at a rear end of the adaptor are connected therethrough. The use of such a connection member allows the sensor cartridge of the present invention to be easily attached/detached to/from the optical equipment.

The disposable sensor cartridge of the present invention may be linked to the LSPR equipment through the adaptor together with the optical fiber sensor mounted in the sensor cartridge to construct a molecular diagnosis system. In this case, the system may include a light source, a detector, and a signal analysis program on a computer.

FIGS. 9A and 9B illustratively show FO-LSPR equipment on which the sensor cartridge of the present invention is mounted. A light source, a detector, and a signal converter are mounted inside an FO-LSPR device body case, and an insertion hole into which the sensor cartridge of the present invention may be inserted is provided in the outer side of the case. A signal analysis program is installed on a computer present at an upper end of the FO-LSPR device body case.

The body case may be manufactured with a size of approximately 180 mm×90 mm×120 mm for point-of-care testing (POCT), and the size may vary depending on the purpose or need. The sensor cartridge of the present invention corresponding to the body case may, for example, have a size of 80 mm×10 mm×25 mm, and the size of the sensor cartridge may vary depending on the purpose or need.

In the FO-LSPR system, when the optical fiber is irradiated with light from a light source, the detector senses the light returning after reaching the metal nanoparticles present at the end of the optical fiber mounted in the sensor cartridge, and a computer program analyzes the light using a USB voltage measurement module device (for example, commercially available Yocto-milliVolt-Rx, and the like) configured to convert these analog signals into digital signals and displays the analysis results.

Therefore, the optical fiber sensor member of the present invention and the sensor cartridge in which the optical fiber sensor member is mounted may detect the presence/absence of the target material with high sensitivity by analyzing transmitted signals of the optical fiber according to the presence/absence of the target material in the sample in conjunction with the FO-LSPR equipment.

The sensor cartridge of the present invention corresponds to a conventional FO-LSPR fluid channel sensor unit. In the related art, the fluid channel sensor unit was basically formed on a slide glass using semiconductor materials such as PDMS, and the like. The fluid channel sensor unit is integrally formed with an FO-LSPR device, and an optical fiber has to be cut for the separation from an optical detection device present at a rear end of the fluid channel sensor unit. In addition, an optical fiber has to be connected using a fusion device for the connection of a new fluid channel sensor unit to the optical detection device.

Thus, the fluid channel sensor unit has problems regarding inconvenience in use and signal stability caused by variations or errors in signals. Also, the fluid channel sensor unit has problems in that manufacturing costs are high due to the use of expensive PDMS materials and mass-production is difficult because it is manufactured using a PDMS material and then attached onto a slide glass. Further, the fluid channel sensor unit has drawbacks in that it is difficult to hold and carry because a sensor exposed to the outside, and thus should be limited to laboratory equipment, and there is a complication of using a syringe pump to inject and wash a sample in the sensor unit of the fluid channel.

Because the sensor cartridge of the present invention is shaped using a general high-molecular resin such as polystyrene, polytetrafluoroethylene, PVC, polypropylene, polyethylene, polycarbonate, polyethylene terephthalate, it has advantages in that it has low manufacturing costs and is easily mass-produced because it is easy to manufacture a mold. Also, it has advantages in that it is possible to easily attach/detach the sensor cartridge to/from an optical device present at a rear end of the sensor cartridge using a connection part such as an adaptor, and it may be conveniently used because a sample or a washing solution may be injected through an injection port of the sensor cartridge using a simple tool such as a pipette and the like. Further, it has advantages in that it may be conveniently applied while preventing a waste fluid from overflowing to external environments during the injection of the sample or washing solution because a reservoir capable of storing a waste fluid is provided in the cartridge body itself, and that it is suitable for disposable use and disposal.

Further, the conventional fluid channel sensor is made of a transparent material, and thus may be used only in a dark room because the fluid channel sensor is sensitive to light. Conversely, the sensor cartridge of the present invention has an advantage in that it may be used anywhere indoors and outdoors because it has a material and structure capable of blocking light on its own.

One embodiment of still another aspect of the present invention is a biomolecular diagnosis system using FO-LSPR, which includes the above-described disposable sensor cartridge and an optical fiber sensor member mounted in the disposable sensor cartridge.

In the biomolecular diagnosis system, an end of an optical fiber sensor is exposed to an environment in which a sample and a reporter molecule to which metal nanoparticles are attached are present in the reaction chamber. When light irradiated from a light source reaches the end of the optical fiber through a connector, depending on the reflective index according to the reaction condition between a ligand attached to the optical fiber and an analyte in the sample, reflected light is received by the detector, and then the detector converts the amount of light into a sensor output value. Accordingly, the presence of the target material may be determined based on the change in output signal intensity value of the sensor.

A biomolecular diagnosis system of the present invention may be configured by mounting an optical fiber sensor member, to which the metal nanoparticles having a reporter molecule attached in the sensor cartridge, and connecting the optical fiber sensor member to an optical detection device such as an FO-LSPR device. In particular, the biomolecular diagnosis system of the present invention including the optical fiber sensor member and the sensor cartridge are conveniently used as small-scale POCT equipment.

Hereinafter, the present invention will be described in further detail through preferred embodiments. However, it should be understood that the preferred embodiments are illustrative in all respects and not restrictive.

EXAMPLES

Example 1: Induction of Non-Specific DNase Activation After Cleavage of Human Papilloma Viral DNA by Cas12a To recognize and cleave human papillomavirus (HPV) DNA, a Cas12a protein (NEB) and crRNA (crispr RNA) were primarily reacted to bind to each other.

The crRNA was synthesized at Integrated DNA Technologies (IDT), and a sequence of the crRNA is as follows:

```
HPV16 crRNA
                                         (SEQ ID NO: 1)
5'-UAAUUUCUACUAAGUGUAGAUUGAAGUAGAUAUGGCAGCAC-3'
```

The sequence recognizes and binds to the L1 gene region of human papillomavirus, and has a protospacer adjacent motif (PAM) sequence "TTTC" positioned at the 5' end. The crRNA synthesized for the binding reaction was diluted to a concentration of 300 nM, and 9 μL of crRNA (300 nM), 3 μL of Cas12a (1 μM), 9 μL of a buffer (50 mM NaCl, 10 mM Tris-HCl, 10 mM MgCl$_2$, 100 μg/mL BSA, pH 7.9), and 60 μL of DEPC-H$_2$O were added until a total volume of the reaction solution reached 81 μL. This solution was reacted at 25° C. for 10 minutes so that the crRNA was allowed to bind to the Cas12a.

The reaction solution was divided into three tubes at 27 μL per tube. Then, 3 μL of ddH$_2$O, 3 μL (300 ng) of a PCR fragment having the L1 region of HPV16, and 3 μL (300 ng) of a PCR fragment having the L1 region of HPV18 were added to tubes 1 to 3, respectively.

The PCR fragment used in the reaction was obtained by PCR amplification of a nucleic acid oligomer having the L1 region of HPV16 or HPV18 (as the standard product for in-vitro diagnostic medical devices, human papillomavirus (HPV) L1 DNA Human Papillomavirus L1 DNA Code No.: 08/023 [Version 2.0, 2013], the Ministry of Food and Drug Safety, Republic of Korea). The PCR reaction was performed using the following: 4 μL of dNTPs (10 mM), 10 μL of a forward primer (10 μM), 10 μL of a reverse primer (10 μM), 3 μL of a template DNA oligomer (100 ng/μl), 40 μL of a 5× Phusion HF buffer (NEB), 3 μL of Phusion DNA polymerase (NEB), and 130 μL of ddH$_2$O were added until a total volume of the reaction solution reached 200 μL. The PCR reaction conditions were 98° C. for 2 minutes at the beginning, 98° C. for 15 seconds, 55° C. for 30 seconds, and 72° C. for one minute and 40 seconds repeated for 30 cycles, and then 72° C. for 10 minutes for the last cycle. The primer sequences used here are as follows:

```
         Forward primer
                                   (SEQ ID NO: 2)
         5'-AAGGGCGAAAAACCGTCTAT-3'

Reverse primer
                                   (SEQ ID NO: 3)
         5'-TACCGGGTTGGACTCAAGAC-3'
```

After the PCR reaction, the PCR fragments were separated using DNA Clean & Concentrator 5 (Zymo Research), and then used for the reaction with the above-described Cas12a-crRNA polymer. As well as the control (ddH₂O), each human papillomavirus DNA amplified by PCR, and the Cas12a-crRNA polymer were reacted at 37° C. for 10 minutes.

In this reaction, the Cas12a-crRNA polymer was bound to a sequence of the HPV16 PCR fragment, and cleaved the target DNA. Accordingly, to confirm whether the non-specific DNase activity of Cas12a was induced, 3 μL of 40-mer ssDNA (20 pmol/μL) was added to the three tubes. The sequence of the 40-mer single-stranded DNA is as follows. The single-stranded DNA was synthesized at Integrated DNA Technologies (IDT), and was designed based on the poly T sequence widely used in substrate DNA having non-specific DNase activity.

```
40-mer single-stranded DNA
                              (SEQ ID NO: 4)
5'-TTTTATTTTATTTTATTTTATTTTATTTTATTTTATTTTA-3'
```

Each of the tubes was reacted at 37° C. for 30 minutes and 60 minutes, and 10 μL of the reaction solution was electrophoresed on a polyacrylamide gel to check the cleavage of the substrate DNA. As a result, as shown in FIG. 10, it was confirmed that the 40-mer single-stranded DNA was cleaved only when HPV16 PCR fragment was present, indicating that the non-specific DNase activity of Cas12 was induced. In this case, it was found that 30 minutes was sufficient for the reaction time under the given conditions.

Example 2: Preparation of Optical Fiber (FO-LSPR) Sensor to Which Nucleic Acid Oligomer Is Attached To bind metal nanoparticles to an optical fiber and attach the 40-mer single-stranded DNA of SEQ ID NO: 4 to the metal nanoparticles, a reaction was performed, as follows.

A multi-mode optical fiber (AFS105/125Y, Thorlabs, USA) was immersed for 20 minutes in a Piranha solution containing sulfuric acid (95% H₂SO₄, Daejung Chemicals & Metals Co., Ltd., Korea) and hydrogen peroxide (34.5% H₂O₂, Samchun Chemicals Co., Ltd., Korea) at a volume ratio of 4:1. The optical fiber was washed with isopropanol and deionized distilled water for 5 minutes, and then immersed for 90 minutes in a 5% (v/v) 3-(ethoxydimethyl-silyl)-propylamine (APMES, 97%, Sigma Aldrich, USA) solution.

The optical fiber activated with an amine group through the above process was immersed for 30 minutes in a colloidal solution including carboxyl nanogold (AuNP, AULB50, nanoComposix, USA) having a diameter of 50 nm to bind the gold nanoparticles to the optical fiber by electrostatic interaction Mae et al., Micro and Nano Syst Lett (2019) 7:171.

To activate a carboxyl group of the gold nanoparticles, a coupling reagent (0.2 M N-(3-dimethylaminopropyl)-N'-carbodiimide; EDC, e1769, Sigma, USA) and an aqueous solution of 0.2 M N-hydroxysuccinimide (NHS, 56485, Sigma, USA) were simultaneously introduced into 1 mL of a 10 mM HEPES buffer (pH 6.0), and the optical fiber to which the gold nanoparticles were attached was reacted for 60 minutes. To attach an amine-modified 40-mer oligomer (custom-made at IDT) of SEQ ID NO: 4 to the gold nanoparticles, the optical fiber to which the gold nanoparticles were bound through the above-described manufacturing process was immersed in 500 μL of a 10 nM 40-mer solution dissolved in a 5 mM potassium phosphate buffer (pH 7.4) and 0.5% polyethylene glycol (PEG20K, 8.18897.1000, Sigma), and then reacted for 60 minutes.

Example 3: Evaluation of Trans-Cleavage Activity of CRISPR-Cas System Using FO-LSPR Sensor to Which Nucleic Acid Oligomer Is Attached The optical fiber manufactured in Example 2, to which the 40-mer oligomer was attached, was stored in a Cas12a reaction buffer (10 mM Tris-HCl, pH 7.9 with 10 mM MgCl₂, 100 μg/m: BSA, and 50 mM NaCl) until use. The optical fiber member to which the 40-mer oligomer was attached was assembled into the ALFS-C1 cartridge (Advanced Label-free Sensor-Cartridge 1, Korean Patent Application No. 2020-0108337) manufactured by the present inventors, which was connected to the sensor analyzer (ALFS-A, Advanced Label-free Sensor-Analyzer, Korean Patent Application No. 2021-0013458) manufactured by the present inventors by means of an adaptor, and then filled with a Cas reaction buffer. The Cas12a (EnGen Lba Cas12a (Cpf1), M0653S, NEB, USA) reaction conditions were established based on the following two reference materials. Chen et al., Science 360, 436-439 (2018) and New England Biolabs protocols: In vitro digestion of DNA with EnGen Lba Cas12a (Cpf1) (M0653)|NEB.

30 nM Cas12a and 30 nM HPV 16 crRNA were pre-incubated at 25° C. for 10 minutes in 48 μL of a Cas12a reaction buffer. Two μL of an HPV16 DNA oligomer (as the standard product for in-vitro diagnostic medical devices, human papillomavirus (HPV) L1 DNA Human Papillomavirus L1 DNA Code No.: 08/023 [Version 2.0, 2013], the Ministry of Food and Drug Safety, ROK) (containing $10^5 10^4$, $10^3$, $10^2$, 0 copies for each reaction) was added to initiate the reaction, and incubated at 37° C. for 10 minutes. To cleave the 40-mer oligomer attached to the optical fiber, 50 μL of the reaction mixture including the incubated Cas12a was injected into the ALFS-C1 cartridge, and reacted. After 10 minutes, 1 mL of a Cas12a reaction buffer was added to terminate the reaction.

The sensor analyzer is a portable LSPR tester for ultra-precise measurement, that is, a device for analyzing the intensity of light reflected from the sensor cartridge ALFS-C1. The inner part of the sensor analyzer includes a laser unit configured to irradiate a laser, a reflected light control unit configured to control the intensity of reflected light so that the intensity of incident light entering the inner part of the sensor cartridge and the intensity of reflected light reflected from the inner part of the sensor cartridge are at a ratio of 1:3, and a reflected light measurement unit configured to measure the intensity of the reflected light and convert the measured intensity into a digital form of voltage. Also, the Yocto-Visualization program (Yocto Company, GB) was used as software for analysis. The experimental results obtained by irradiating a laser at a wavelength of 640 nm are as follows.

The net changes in output intensities of the optical fibers according to the copy number of HPV16 DNA measured using the above device are listed in Table 1.

TABLE 1

| Copy No.$^a$ | Initial I$^b$ | Final I$^c$ | Delta I$^d$ |
|---|---|---|---|
| 100,000 | −0.154 | −9.901 | 9.747 |
| 10,000 | 0.177 | −7.508 | 7.685 |
| 1,000 | 0.293 | −6.611 | 6.904 |

TABLE 1-continued

| Copy No.[a] | Initial I[b] | Final I[c] | Delta I[d] |
|---|---|---|---|
| 100 | −0.01 | −4.718 | 4.708 |
| 0 | 0.205 | 1.319 | −1.114 |

[a]Copy number of HPV 16 DNA oligomer
[b]Initial mean intensity value normalized for one minute (from −1 to 0 minute)
[c]Final mean intensity value normalized for one minute (from 9 to 10 minutes)
[d]Net changes in intensity calculated as Initial I − Final I As shown in Table 1, the normalized initial mean intensity I (Initial I) is defined as a mean value of output intensity values of the optical fibers to which the 40-mer ssDNA-attached gold nanoparticles were bound for one minute prior to the injection of the reaction mixture. The normalized final mean intensity I (Final I) is defined as a mean value of output intensity values of the optical fibers to which the 40-mer ssDNA-attached gold nanoparticles were bound, in which the cleavage reaction by Cas12a occurs from 9 minutes to 10 minutes after the injection of the reaction mixture. The difference between the Initial I and the Final I means that the presence of the HPV 16 L1 sequence as the target sequence activates the trans-cleavage ability of CRISPR-Cas12a to decrease the size of the ssDNA oligomer.

Delta I, which is a net change in output intensity of the optical fiber, is calculated by subtracting the Final I value from the Initial I value. As shown in Table 1 and FIG. 12, it was found that the Delta I value was proportional to the copy number of HPV16 DNA.

FIGS. 13 to 17 sequentially show sensograms of the trans-cleavage activities of CRISPR-Cas12 according to the amount of HPV16 DNA (having a total copy number of $10^5$, $10^4$, $10^3$, $10^2$ and 0 in the reaction solution) (FIGS. 13 to 17). This is a normalized intensity that relatively denotes to what extent the substrate oligomer of the optical fiber is cleaved after the trans-activation of Cas12a starting from 0 minute. As shown in FIGS. 13 to 17, it can be seen that the output intensity value varied according to the copy number of the target nucleic acid. Therefore, it was confirmed that the system for detecting a target nucleic acid operates well using the FO-LSPR and CRISPR-Cas12 systems of the present invention.

The system of the present invention can detect even 100 copies of the target DNA in 50 μL of the reaction solution, which corresponds to an attomolar (aM) concentration of the target DNA. Therefore, the system of the present invention has very high sensitivity because the system can detect a very small amount of the target molecule. Also, a total of approximately 30 minutes (including approximately 15 minutes required for pre-incubation with the sample for Cas protein activation, and then approximately 15 minutes required for reading the output signal intensity using the LSPR equipment after the reaction product is brought into contact with the optical fiber sensor) was sufficient for deducing results. Therefore, the system of the present invention may rapidly detect the biomolecule in the sample.

Also, the molecular diagnosis system including the FO-LSPR sensor having metal nanoparticles to which the nucleic acid oligomer of the present invention is attached may also meet the accuracy distinguished from existing immunodiagnosis as well as the above-described sensitivity and speed, and thus may be very effectively used in the modern world in which infectious diseases such as COVID19 cases are spreading.

As described above, while the present invention has been described with reference to embodiments thereof, it should be understood by those skilled in the art or those of ordinary skill in the art that various modifications and changes can be made to the present invention without departing from the spirit and technical scope of the present invention described in the accompanying claims. Accordingly, the technical scope of the present invention is not limited to the content described in the detailed description of the specification, but should be defined by the claims. Therefore, it should be understood that the embodiments described above are illustrative in all respects and not restrictive.

The invention claimed is:

1. A method for detecting a target nucleic acid in a test sample, comprising:

a) contacting a CRISPR RNA, which binds to a target nucleic acid, and a Cas protein, with a test sample isolated from a living body so that the CRISPR RNA and the Cas protein are allowed to react with the test sample to obtain a reaction product;

b) contacting the reaction product with a fiber optics-localized surface plasmon resonance (FO-LSPR) sensor containing metal nanoparticles having nucleic acid oligomers attached thereto; and c) irradiating the sensor with light to measure a reflective index intensity change value of an FO-LSPR output signal to detect the presence of the target nucleic acid in the test sample.

2. The method of claim 1, wherein the target nucleic acid is selected from the group consisting of dsDNA, ssDNA, and ssRNA, and the Cas protein is selected from the group consisting of Cas12a, Cas13a, and Cas14.

3. The method of claim 1, wherein the Cas protein is Cas12a, the CRISPR RNA has a base sequence set forth in SEQ ID NO: 1, and the target nucleic acid is HPV16 dsDNA.

4. The method of claim 1, wherein the method further comprises comparing the FO-LSPR output signal with an FO-LSPR output signal value from a control sample.

5. The method of claim 1, wherein the CRISPR RNA is a mixture of RNAs that are able to bind to several sites of the target nucleic acid, respectively.

\* \* \* \* \*

SEQUENCE LISTING

```
<160> NUMBER OF SEQ ID NOS: 4

<210> SEQ ID NO 1
<211> LENGTH: 41
<212> TYPE: RNA
<213> ORGANISM: Artificial Sequence
<220> FEATURE:
<223> OTHER INFORMATION: HPV16 crRNA

<400> SEQUENCE: 1
uaauuucuac uaaguguaga uugaaguaga uauggcagca c                    41

<210> SEQ ID NO 2
<211> LENGTH: 20
<212> TYPE: DNA
<213> ORGANISM: Artificial Sequence
<220> FEATURE:
<223> OTHER INFORMATION: forward primer

<400> SEQUENCE: 2
aagggcgaaa aaccgtctat                                           20

<210> SEQ ID NO 3
<211> LENGTH: 20
<212> TYPE: DNA
<213> ORGANISM: Artificial Sequence
```

-continued

```
<220> FEATURE:
<223> OTHER INFORMATION: reverse primer

<400> SEQUENCE: 3
taccgggttg gactcaagac                                              20

<210> SEQ ID NO 4
<211> LENGTH: 40
<212> TYPE: DNA
<213> ORGANISM: Artificial Sequence
<220> FEATURE:
<223> OTHER INFORMATION: reporter

<400> SEQUENCE: 4
ttttatttta ttttatttta ttttatttta ttttatttta                       40
```